(12) United States Patent
Moore et al.

(10) Patent No.: US 10,213,362 B2
(45) Date of Patent: Feb. 26, 2019

(54) PORTABLE HYDRO-THERMAL THERAPY SYSTEM FOR USE WITH A VESSEL FOR CONTAINING WATER AND METHOD FOR USE OF SAME

(71) Applicants: Mark Moore, Waco, TX (US); Walter Abercrombie, Waco, TX (US)

(72) Inventors: Mark Moore, Waco, TX (US); Walter Abercrombie, Waco, TX (US)

(73) Assignee: Hobson A. Howell, Woodway, TX (US)

( * ) Notice: Subject to any disclaimer, the term of this patent is extended or adjusted under 35 U.S.C. 154(b) by 807 days.

(21) Appl. No.: 13/776,624

(22) Filed: Feb. 25, 2013

(65) Prior Publication Data

US 2013/0226044 A1   Aug. 29, 2013

Related U.S. Application Data

(60) Provisional application No. 61/603,210, filed on Feb. 24, 2012.

(51) Int. Cl.
*A61H 33/00* (2006.01)
*A61F 7/00* (2006.01)

(52) U.S. Cl.
CPC ....... *A61H 33/0091* (2013.01); *A61F 7/0085* (2013.01); *A61H 33/0087* (2013.01); *A61H 33/0095* (2013.01); *A61F 2007/0029* (2013.01); *A61F 2007/0039* (2013.01); *A61F 2007/0056* (2013.01); *A61F 2007/0086* (2013.01); *A61H 2201/0157* (2013.01); *A61H 2201/0214* (2013.01); *A61H 2201/0242* (2013.01)

(58) Field of Classification Search
CPC ............ A61H 33/0087; A61H 33/0091; A61H 33/0095; A61H 2201/0242; A61H 2201/0214; A61F 7/0085; A61F 2007/0029; A61F 2007/0056; A61F 2007/0086; A61F 2007/0039; A61F 2201/0157; A61F 2201/0214; A61F 2201/0242
See application file for complete search history.

(56) References Cited

U.S. PATENT DOCUMENTS

| 3,911,505 A | 10/1975 | Zaborowsky |
| 3,916,911 A | 11/1975 | Sauder et al. |

(Continued)

*Primary Examiner* — Colin W Stuart
*Assistant Examiner* — Douglas Sul
(74) *Attorney, Agent, or Firm* — Scott T. Griggs; Griggs Bergen LLP

(57) ABSTRACT

A portable hydro-thermal therapy system for use with a vessel for containing water and method for use of the same are disclosed. In one embodiment, the portable hydro-thermal therapy system includes a mobile trailer having a platform to achieve point-to-point haulage thereof. A cool water supply device having inlet and outlet port is mounted on the platform. The cool water supply device includes a water circulation path from the inlet port to the outlet port, a water pump coupled to the water circulation path, and a refrigeration cycle contained within the cool water supply device. A thermostat and water pump may cooperate in combination to provide water between about 50° F. and about 55° F. The water circulation path is thermally proximate to the evaporator coil in order to cool the water being pumped through the water circulation path to and from the vessel by way of inlet and outlet tubing.

7 Claims, 2 Drawing Sheets

(56) References Cited

U.S. PATENT DOCUMENTS

| | | | |
|---|---|---|---|
| 4,047,522 A * | 9/1977 | Plugge | 601/157 |
| 4,099,522 A * | 7/1978 | Alenares | A61H 35/006 |
| | | | 601/156 |
| 4,149,529 A * | 4/1979 | Copeland | A61H 9/0078 |
| | | | 601/151 |
| 4,192,297 A * | 3/1980 | Labrecque | A61H 9/00 |
| | | | 601/166 |
| 4,630,599 A | 12/1986 | Perovick et al. | |
| 4,844,072 A * | 7/1989 | French et al. | 607/104 |
| 4,945,901 A * | 8/1990 | Burcke, Jr. | A61H 23/0245 |
| | | | 601/157 |
| 5,227,704 A * | 7/1993 | Erdman | 318/400.34 |
| 5,245,221 A | 9/1993 | Schmidt et al. | |
| 5,806,335 A | 9/1998 | Herbert et al. | |
| 5,865,841 A * | 2/1999 | Kolen et al. | 607/104 |
| 6,003,166 A | 12/1999 | Hald et al. | |
| 6,086,609 A | 7/2000 | Buckley | |
| 6,176,869 B1 * | 1/2001 | Mason | A61F 7/02 |
| | | | 601/15 |
| 6,401,273 B1 | 6/2002 | Fung et al. | |
| 6,551,347 B1 * | 4/2003 | Elkins | A61F 7/0085 |
| | | | 165/46 |
| 7,302,808 B1 | 12/2007 | Teetzel et al. | |
| 7,353,548 B2 | 4/2008 | Bartosik | |
| 7,520,731 B1 | 4/2009 | Landon, II et al. | |
| 7,640,764 B2 | 1/2010 | Gammons et al. | |
| 2003/0114903 A1 * | 6/2003 | Ellingboe | 607/104 |
| 2004/0112991 A1 * | 6/2004 | Rojewski | A61H 33/0087 |
| | | | 239/548 |
| 2006/0288476 A1 * | 12/2006 | Reynolds, II | 4/541.1 |
| 2011/0106023 A1 * | 5/2011 | Lowe | A61F 7/02 |
| | | | 604/291 |
| 2011/0120684 A1 * | 5/2011 | Filho | 165/163 |

* cited by examiner

PORTABLE HYDRO-THERMAL THERAPY SYSTEM FOR USE WITH A VESSEL FOR CONTAINING WATER AND METHOD FOR USE OF SAME

CROSS-REFERENCE TO RELATED APPLICATION

This application claims priority from Application Ser. No. 61/603,210 entitled "Portable Hydro-thermal Therapy System for Use with a Vessel for Containing Water and Method for Use of Same," and filed on Feb. 24, 2012 in the names of Mark Moore and Walter Abercrombie, which is hereby incorporated by reference for all purposes.

TECHNICAL FIELD OF THE INVENTION

This invention relates, in general, to portable cooling systems and, in particular, to a portable hydro-thermal therapy system for use with a vessel for containing water and a method for use of the same.

BACKGROUND OF THE INVENTION

Acute sports injuries such as sprains, strains and contusions are usually very painful. The use of cold in the treatment of sports injuries, such as acute sports injuries and heat exhaustion, is a well known practice and the immediate application of cold can help reduce the swelling and ease the pain. Typically, bags of ice are maintained on standby at an athletic field or stadium to provide hydrotherapy and cold treatment. A need exists, however, for a system and method that minimize the reliance on bags of ice. There is also a need for systems and methods that provide a portable hydro-thermal therapy system for standby and rapid use at an athletic field and stadium.

SUMMARY OF THE INVENTION

It would be advantageous to achieve a system and method for providing hydro-thermal therapy that minimize the reliance on bags of ice. It would also be desirable to enable an electro-mechanical based solution that would furnish portable hydro-thermal therapy system for standby and rapid use at an athletic field and stadium. To better address one or more of these concerns, in one aspect of the invention, a portable hydro-thermal therapy system and related method are disclosed for use with a vessel for containing water. In one embodiment, a portable hydro-thermal therapy system for use with a vessel for containing water and method for use of the same are disclosed. The portable hydro-thermal therapy system may include a mobile trailer having a platform that is configured for an individual to achieve point-to-point haulage thereof. A cool water supply device having inlet and outlet ports is mounted on the platform. The cool water supply device includes a water circulation path from the inlet port to the outlet port, a water pump coupled to the water circulation path, and a refrigeration cycle contained within the cool water supply device. A thermostat and water pump may cooperate in combination to provide water between about 50° F. (10° C.) and about 55° F. (13° C.). The water circulation path is thermally proximate to the evaporator coil in order to cool the water being pumped through the water circulation path to and from the vessel by way of inlet and outlet tubing.

That is, the product may be a portable chiller unit to facilitate recovery from heat exhaustion and immediate therapy from field injuries. The portable chiller unit is located on a platform that allows for either being pulled by a motorized cart or easily hand pulled. The portable chiller unit circulates water through a customer provided water tank source the individual or individuals are placed in. The portable chiller unit circulates the water down to a specified temperature by a thermostat control. The portable chiller unit therefore replaces the reoccurring need for large and costly amounts of ice; not to mention the constantly reoccurring manual labor resources to utilize the ice. The portable chiller unit may be powered by a 120 volt power cord or a 120 volt power providing generator or even a battery, at the customer's discretion.

In one implementation, the portable chiller unit is comprised of a refrigerant bearing chiller condensing unit, a water circulating evaporator coil, a water pump to circulate the water, a supply/return hose, a thermostat, high/low pressure switches, a water flow switch to prevent the portable chiller unit from operating if the water flow stops, as well as an on/off switch. In one embodiment, the design allows for the thermostat, power switch and water circulation hoses only, to be manipulated by the end user.

The inside portion contains all of the moving mechanical parts and may be accessed by only qualified service repairmen, for safety issues. This facilitates the use of the portable chiller unit by an unlimited number of customers. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1:
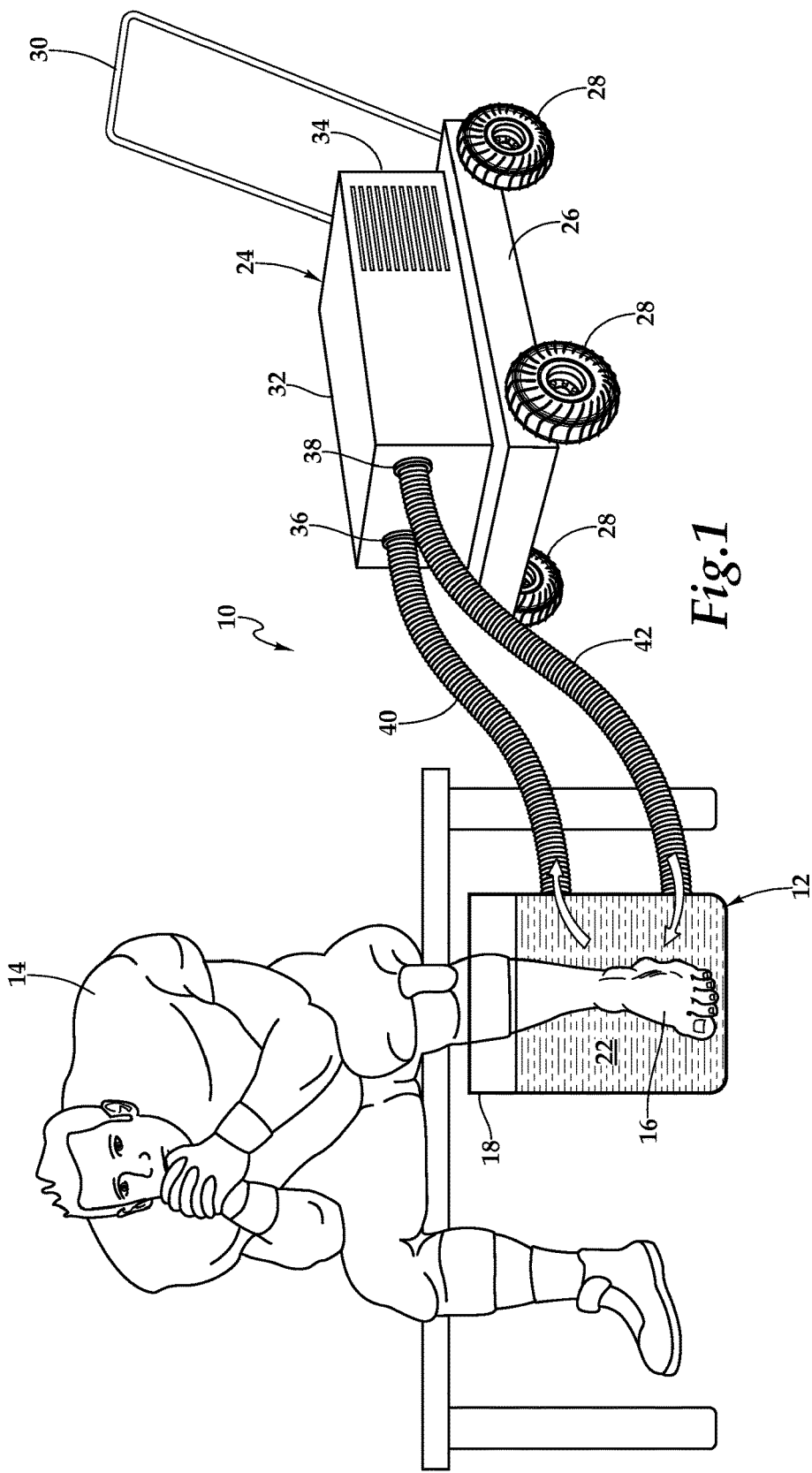
FIG. 1 is a perspective view of one embodiment of an individual utilizing a portable hydro-thermal therapy system for use with a vessel for containing water, wherein a method for use of the same is employed.

Referring to FIG. 1, in one embodiment, a portable hydro-thermal therapy system 10 is being utilized with a vessel 12 by an individual 14 in order to provide immediate relief of an athletic injury 16. The vessel includes an open top 18 having a sufficient opening 20 to permit, in this embodiment, a person or limb to be placed therein. As shown, the vessel 12 contains fluid 22 in the form of water. In this implementation, the portable hydro-thermal therapy system 10, which may be designed as a kit, includes a mobile trailer 24 having a platform 26 that is physically configured for an individual to achieve point-to-point haulage thereof. Wheels 28 are mounted to the platform and, as shown, a handle 30 provides for ease of movement. It should be appreciated that although the particular mobile trailer 24 includes four wheels and a particular handle configuration, other wheel and handle configurations are within the teachings presented herein.

A cool water supply device 32 having a housing 34 is mounted on the platform 26. The cool water supply device 32 has an inlet port 36 and an outlet port 38 placed therein and a water circulation path is defined from the inlet port 36 to the outlet port 38 and, more generally, from the inlet tubing 40 to the outlet tubing 42. As shown, both the inlet tubing 40 and outlet tubing 42 are placed within the vessel 12. It should be appreciated, however, that the inlet tubing 40 and outlet tubing 42 may be integrated or selectively coupled to the vessel 12 in another embodiment, wherein coupling ends are utilized on the inlet tubing 40 and the outlet tubing 42 to selectively couple the hydro-thermal therapy system 10 to the vessel 12.

As depicted, the hydro-thermal therapy system 10 is utilized to facilitate recovery from heat exhaustion and immediate therapy from field injuries. The hydro-thermal therapy system is easily pulled by hand to the injured athlete 14 and the hydro-thermal therapy system 10 circulates water 22 through a customer provided water tank source, such as the vessel 12, where the individual is placed. The hydro-thermal therapy system 10 circulates the water 22 down to a specified temperature by a thermostat control, thereby replacing the reoccurring need for large and costly amounts of ice; not to mention the constantly reoccurring manual labor resources to utilize the ice. It should be understood that although the hydro-thermal therapy system 10 is depicted as heating a vessel on an athletic field, the teachings presented herein are not limited to use with human athletes or vessels on athletic fields. The portable hydro-thermal therapy system may be utilized with other types of animals, such as horses, for example. Further, the portable hydro-thermal therapy system may be used with other bodies of water, including swimming pools, for example.

Figure 2:
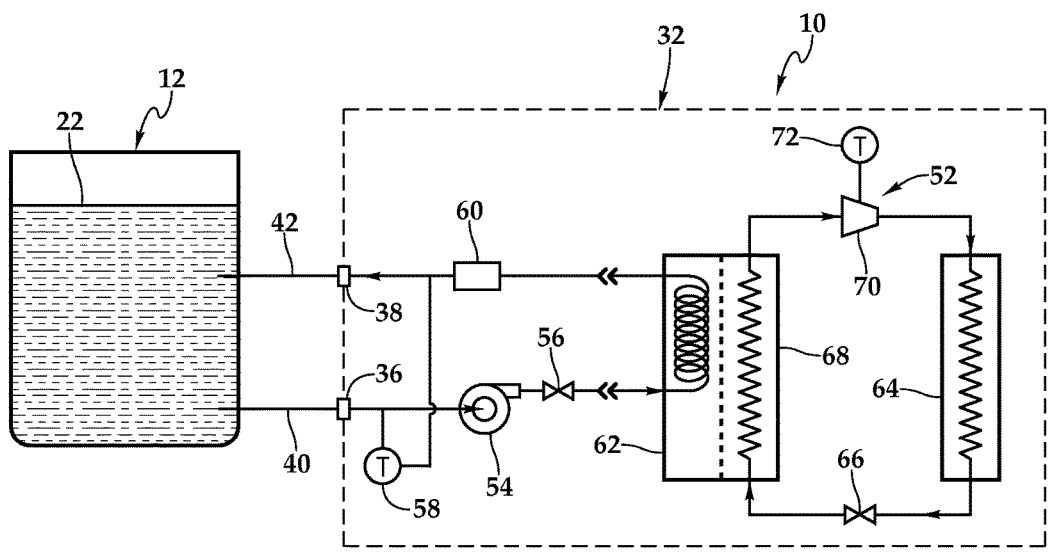
FIG. 2 is a flow diagram of one embodiment of the portable hydro-thermal therapy system depicted in FIG. 1.

FIG. 2 illustrates one embodiment of the portable hydro-thermal therapy system 10, which includes a water circulation path 50 and a refrigeration cycle 52. The water circulation path 50 includes a water pump 54 coupled thereto in order to pump water from the inlet port 36 to the outlet port 38 and from the inlet tubing 40 to the outlet tubing 42, both of which are located in fluid communication with the vessel 12. In one embodiment, the pump 54 is a DC powered, single speed, submersible centrifugal, self-priming pump. In various embodiments, a valve 56 is either a flow control valve, a solenoid operated valve, or a diverter valve. The outlet tubing 42 connected to the outlet port 38, in one embodiment, includes a temperature indicator or thermometer 58 that provides indication of the temperature of the fluid circulating into the vessel 12 or therefor in which case the thermostat 58 is coupled to both the inlet tubing 40 and the outlet tubing 42. A flow restrictor 60 may be coupled to the outlet tubing increases the back-pressure in order to ensure proper pressure is maintained. A water thermal exchange chamber 62 is located at the junction of the inlet tubing 40 and the outlet tubing 42.

The refrigeration cycle 52 is contained within the cool water supply device 32, to include a refrigerant, such as Freon, circulating through a condensing coil 64, an expansion valve 66, an evaporator coil 68, and a compressor 70 under the thermal control of a thermostat 72, which may be integrated with or the same as thermostat 58, both of which are the control of a controller as will be discussed in further detail hereinbelow. The thermostat 70 and water pump 54 cooperate in combination to preferably provide water between about 50° F. (10° C.) and about 55° F. (13° C.). The water circulation path 50—and particularly the water temperature exchange chamber 62—is located thermally proximate to the evaporator coil 68 or partially integrated therewith in order to cool the water 22 being pumped through the water circulation path 50. The inlet tubing 40 is coupled to the inlet port 36 and outlet tubing 42 is coupled to the outlet port 38 such that the cool water supply device 32 is configured to forceably circulate water through the vessel 12.

With respect to one embodiment of the refrigeration cycle 52, a circulating refrigerant such as Freon enters the compressor 70 as a vapor. The vapor is compressed at constant entropy and exits the compressor 70 superheated. The superheated vapor travels through the condenser 64, which first cools and removes the superheat and then condenses the vapor into a liquid by removing additional heat at constant pressure and temperature. The liquid refrigerant goes through the expansion valve 66, which may be a throttle valve, where its pressure abruptly decreases, causing flash evaporation and auto-refrigeration of, typically, less than half of the liquid, in one embodiment. That results in a mixture of liquid and vapor at a lower temperature and pressure. The cold liquid-vapor mixture then travels through the evaporator coil 68 or tubes and is completely vaporized by cooling the warm water or warmer water within the water thermal exchange chamber 62 proximate to and in contact with the evaporator coil or tubes 68. The resulting refrigerant vapor returns to the compressor inlet to complete the thermodynamic cycle.

The following table, Table I, describes exemplary, non-limiting characteristics of one prototype built in accordance with the teachings presented herein.

TABLE I

Exemplary Design Details

| Parameter | Exemplary Value |
| --- | --- |
| Design Water Flow | 7 gallons/minute |
| Design Superheat | 10° F. (−12° C.) |
| Design Sub-cooling | 6° F. (−14° C.) |
| Design Minimum Water Temperature | 50° F. (10° C.) |
| Design Maximum Water Temperature | 80° F. (27° C.) |
| Refrigerant | No. 404 |
| Maximum Gallons Cooling | 350 gallons |
| Controls | 24 V, Main Power 115 V, 15 A |
| Safety Controls | High & Low Pressure Switch Flow Switch |
| Unit Design Cooling Capabilities to Withstand | 105° F. (41° C.) |
| Platform Design | Moderate to Rough Terrain |
| Design Weight | 200 lbs. |

Figure 3:
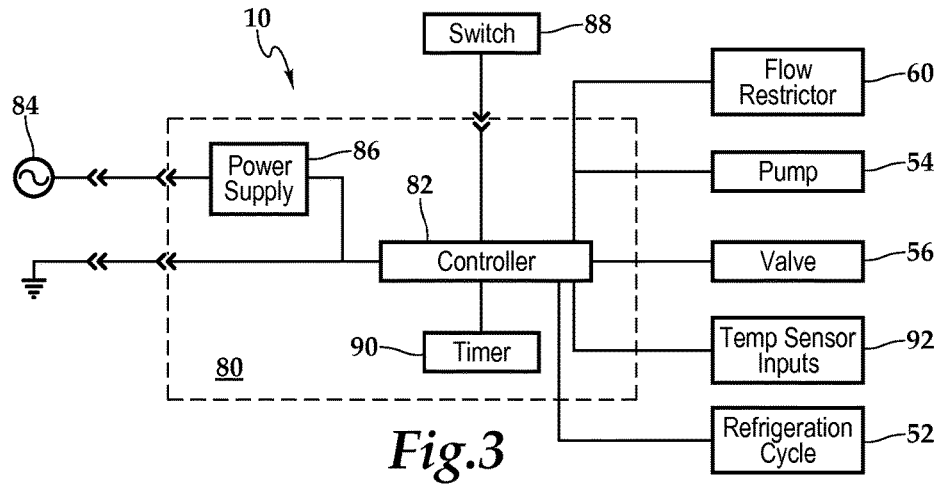
FIG. 3 is a block schematic diagram of one embodiment of the portable hydro-thermal therapy system depicted in FIG. 1.

FIG. 3 illustrates one embodiment of the portable hydro-therapy system 10, which includes a control circuit 80 having a controller 82 that is configured to operate from either a standard AC power source 84 (as shown) or a battery, such as an automotive battery or battery pack. An AC power cable may connect the AC power source 84 to a power supply 86 that converts the AC power to a DC voltage that powers the remainder of the system 10. If it is desirable to use DC power, a DC power cable may connect the battery to the system 10.

A switching unit 88 may be mounted to the housing of the portable hydro-thermal therapy device 10 or, in another embodiment, the switching unit 88 may be remote by way of a transmitter and receiver combination. In still another embodiment, the switching unit 88 may include both a mounted component and a remote component. The switching unit 88 is coupled to a switching unit that communicates with the controller 82. The control circuit 80 includes a timer 90 in communication with the controller 82. In various embodiments, the switching unit 88 may include one or more of a start switch, a stop switch, a flow rate switch, and/or a speed switch.

In the illustrated embodiment, the controller 82 receives an input from a temperature sensor 92, such as one or more of the thermometer 58 and thermostat 72 and controls the water pump 54 and the valve 56, as well as the flow restrictor 60 and other components of the water circulation cycle or path 50. In addition, the controller controls the refrigeration cycle 52, including each of the components therein. In this embodiment, the controller 82 is a device that controls a process through one or more outputs, based on one or more inputs, to execute such functions as selectively providing power to the pump 54 in response to input signals, such as temperature signals, refrigeration signals, pump signals, and flow restriction signals, for example. In other embodiment, the portable hydro-thermal therapy system 10 does not monitor the temperature of the fluid or control the valve. In such exemplary embodiments, the switching unit or switch 88 operates the controller or directly operates the pump 54. In one such embodiment, the switching unit 88 includes a timer and the switching unit provides a control signal for a predetermined time. Further operational embodiments will now be discussed.

In one embodiment, the portable hydro-thermal therapy system 10 operates for a pre-determined time period whenever the system 10 is turned ON. In such an embodiment, the switching unit 90 includes a switch for turning the pump ON. The controller 82 starts the pump in response to the switching unit 88. The controller 82 also starts the timer 90, which provides the controller 82 with a stop signal after a pre-determined time period. The controller 82 stops the pump 54 when the controller receives the stop signal from the timer 90. In such an embodiment, the controller 82 is a device that interrupts power to the pump 54 in response to a signal from the switching unit 88. In various such embodiments, the switching unit 88 includes a timer such that the signal from the remote switching unit is enabled for a specified period, thereby operating the pump for such a period.

In another embodiment, the portable hydro-thermal therapy system 10 operates with a selected duty cycle, that is, the pump 54 cycles at a selected rate to control the time that the water flows to the water thermal exchange chamber 62, which as previously discussed may be at least partially integrated with the evaporator coils 68. In such an embodiment, the selected duty rate alternates at a low frequency, for example, the duty rate varies between having the pump 54 operate for ten seconds every minute to having the pump 54 operate for four minutes out of every five minutes. In such an embodiment, the switching unit includes a switch for turning the system 10 ON and another switch for controlling the duty rate. The controller 82 reads the switching unit and the timer to control the pump to have the selected duty cycle.

In one such embodiment, the portable hydro-thermal therapy system 10 operates with a high frequency duty cycle, that is, the pump 54 cycles at a selected rate to control the time that the water flows to the water temperature exchange chamber 62 and the frequency of the cycles is sufficiently high that the fluid flow appears to be constant to the user of the water temperature exchange chamber 62. That is, the high frequency duty cycle pulsing of the pump does not result in a user detectable pulsing or throbbing at the water temperature exchange chamber 62. The controller 82 generates a pulse stream that powers the pump 54. In this embodiment, the pump 54 is a centrifugal pump and the motor of the pump receives power in full voltage pulses that have a time width of between 1 millisecond and 1 second, for example. The flow from the pump 54 increases when the pulse powers the pump and the flow ramps down after the pulse stops. The centrifugal pump is contrasted to a positive displacement pump, which has a flow profile resembling a square wave.

In another such embodiment, the pump 54 is run continuously and the valve 56 is operated to meet the duty cycle requirements. In one such embodiment, the valve 56 is operated by the controller to open and close, with a specified frequency, to control the flow to the water temperature exchange chamber 62. In such an embodiment, the selected duty rate alternates at a high frequency, for example, the valve cycles several times a second. The switching unit 88 includes a switch for turning on the system 10 and another switch for controlling the duty rate. In another such embodiment, the valve is a manual operated valve and the valve is adjusted for the desired flow rate.

In yet another embodiment, the portable hydro-thermal therapy system 10 operates at a specified temperature. In one embodiment, the flow rate to the water temperature exchange chamber 62 is adjusted such that the average temperature of the water temperature exchange chamber 62 is maintained at a set point. As described above, the flow rate is controlled by pulsing the pump motor 54, by pulsing the control valve 56, or by manually controlling the valve.

In another embodiment, the portable hydro-thermal therapy system 10 provides contrast therapy in which a patient is exposed to consecutive changes of localized temperature therapy. In this embodiment, the controller 82, in combination with the timer 90, applies cool water flow to the vessel for intermittent periods. Some studies demonstrate that after four changes, the body adjusts to the intermittent temperature changes.

Figure 4:
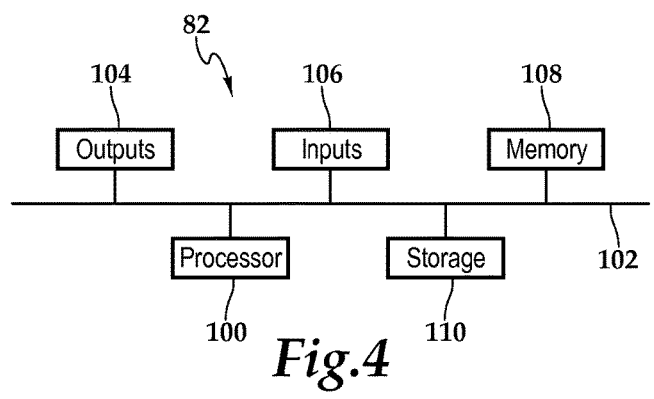
FIG. 4 is a block schematic diagram of one embodiment of a controller depicted in FIG. 3.

FIG. 4 depicts one embodiment of the controller 82 in which the controller is schematically depicted to include a computer-based architecture including a processor 100 coupled to a bus 102 having outputs 104, inputs 106, memory 108, and storage 110 interconnected therewith. In one embodiment, the controller 82 includes the memory 108, which is accessible to the processor 100. The memory 108 includes processor-executable instructions that, when executed cause the processor to execute instructions for measuring temperature, selectively activating the pump, and selectively activating the refrigeration cycle to achieve a change in temperature of the water flowing through the water circulation path based on matching the desired temperature with the rate of flow and refrigeration cooling coefficient. It should be appreciated that other instruction sets corresponding to the operational and functional modes enumerated in FIG. 3 are within the programming capabilities taught herein.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A portable hydro-thermal therapy kit, comprising:
a vessel having an open top, the vessel being an open water tank source for a cool water supply water device having water;
a portable hydro-thermal therapy system comprising:
  a mobile trailer having a platform, the mobile trailer including four wheels and a handle mounted to the platform, the mobile trailer physically configured for an individual to achieve point-to-point haulage thereof;
  the mobile trailer having a design weight of about 200 pounds;
    the cool water supply device mounted on the platform, the cool water supply device having an inlet port and an outlet port, the cool water supply device including:
    a closed water circulation path within the cool water supply device defining a path from the inlet port to the outlet port with the open water tank source consisting of a water source,
    a thermometer monitoring the temperature of water pumping into the inlet port, and the thermometer monitoring the temperature of water pumping from the outlet port,
    a water pump coupled to the closed water circulation path, the water pump for pumping water from the inlet port to the outlet port,
    a refrigeration cycle contained within the cool water supply device, the refrigeration cycle including a refrigerant circulating through a condensing coil, an expansion valve, a evaporator coil, and a compressor under the thermal control of a thermostat in communication with the thermometer, and
    the closed water circulation path including a water thermal exchange chamber interposed between the inlet port and outlet port, the water thermal exchange chamber being thermally proximate to the evaporator coil,
    the thermostat and water pump cooperating in combination to provide water between about 50° F. and about 55° F.;
  a flow restrictor secured to an outlet tubing to regulate the back pressure in order to ensure proper pressure is maintained,
  the closed water circulation path being thermally proximate to the evaporator coil in order to cool the water being pumped through the water circulation path;
  inlet tubing coupled to the inlet port, the cool water supply device configured to pump water out of the vessel through the inlet tubing as the sole source of water to the cool water supply device;
  the cool water supply device having a design with flow of about seven gallons/minute with an about 300 gallons cooling capacity;
  the outlet tubing coupled to the outlet port, the cool water supply device configured to pump water into the vessel through the outlet tubing; and
  a controller located within the cool water supply device in communication with the closed water circulation path and the refrigeration cycle, the controller including memory, which is accessible to a processor, the memory includes processor-executable instructions that, when executed cause the processor to execute instructions for measuring temperature via the thermometer, selectively activating the water pump, and selectively activating the refrigeration cycle to achieve a change in temperature of the water flowing through the closed water circulation path based on matching the desired temperature with the rate of flow and refrigeration cooling coefficient in view of the constant pressure maintained by the flow restriction.

2. The portable hydro-thermal therapy system as recited in claim 1, wherein the inlet and outlet tubing further comprise coupling ends for selectively fastening to the vessel.

3. A portable hydro-thermal therapy system for use with a vessel for containing water, the vessel having an open top, the portable hydro-thermal therapy system comprising:
  a mobile trailer having a platform, the mobile trailer including four wheels and a handle mounted to the platform, the mobile trailer physically configured for an individual to achieve point-to-point haulage thereof;
  the mobile trailer having a design weight of about 200 pounds;
  a cool water supply device mounted on the platform, the cool water supply device having an inlet port and an outlet port, the vessel being a water tank source for the cool water supply water device;
  the cool water supply device including:
    a closed water circulation path within the cool water supply device defining a path from the inlet port to the outlet port with the open water tank source consisting of a water source,
    a thermometer monitoring the temperature of water pumping into the inlet port, and the thermometer monitoring the temperature of water pumping from the outlet port,
    a water pump coupled to the closed water circulation path, the water pump for pumping water from the inlet port to the outlet port,
    a refrigeration cycle contained within the cool water supply device, the refrigeration cycle including a refrigerant circulating through a condensing coil, an expansion valve, a evaporator coil, and a compressor under the thermal control of a thermostat in communication with the thermometer, and
    the closed water circulation path including a water thermal exchange chamber interposed between the inlet port and outlet port, the water thermal exchange chamber being thermally proximate to the evaporator coil,
    the thermostat and water pump cooperating in combination to provide water between about 50° F. and about 55° F.;
  a flow restrictor secured to an outlet tubing to regulate the back pressure in order to ensure proper pressure is maintained;
  the water circulation path being thermally proximate to the evaporator coil in order to cool the water being pumped through the water circulation path;
  inlet tubing coupled to the inlet port, the cool water supply device configured to pump water out of the vessel through the inlet tubing as the sole source of water to the cool water supply device;
  the cool water supply device having a design with flow of about seven gallons/minute with an about 300 gallons cooling capacity;

outlet tubing coupled to the outlet port, the cool water supply device configured to pump water into the vessel through the outlet tubing; and a controller located within the cool water supply device in communication with the closed water circulation path and the refrigeration cycle, the controller including memory, which is accessible to a processor, the memory includes processor-executable instructions that, when executed cause the processor to execute instructions for measuring temperature via the thermometer, selectively activating the water pump, and selectively activating the refrigeration cycle to achieve a change in temperature of the water flowing through the water circulation path based on matching the desired temperature with the rate of flow and refrigeration cooling coefficient in view of the constant pressure maintained by the flow restriction.

4. The portable hydro-thermal therapy system as recited in claim 3, wherein the water pump stops for a pre-selected period of time after the pump is started by the controller, the controller being located within the cool water supply device.

5. The portable hydro-thermal therapy system as recited in claim 3, wherein the water pump stops for a pre-selected period of time after the pump is started by the controller.

6. The portable hydro-thermal therapy system as recited in claim 3, further comprising a means for varying a flow rate through the thermal exchange chamber.

7. A portable hydro-thermal therapy kit, consisting of:
a vessel having an open top, the vessel being an open water tank source for a cool water supply water device having water;
a portable hydro-thermal therapy system comprising:
a mobile trailer having a platform, the mobile trailer including four wheels and a handle mounted to the platform, the mobile trailer physically configured for an individual to achieve point-to-point haulage thereof;
the cool water supply device mounted on the platform, the cool water supply device having an inlet port and an outlet port, the cool water supply device including:
a closed water circulation path within the cool water supply device defining a path from the inlet port to the outlet port with the open water tank source consisting of a water source,
a water pump coupled to the closed water circulation path, the water pump for pumping water from the inlet port to the outlet port,
a refrigeration cycle contained within the cool water supply device, the refrigeration cycle including a refrigerant circulating through a condensing coil, an expansion valve, a evaporator coil, and a compressor under the thermal control of a thermostat, and
the closed water circulation path including a water thermal exchange chamber interposed between the inlet port and outlet port, the water thermal exchange chamber being thermally proximate to the evaporator coil, and
the thermostat and water pump cooperating in combination to provide water between about 50° F. and about 55° F.;
the closed water circulation path being thermally proximate to the evaporator coil in order to cool the water being pumped through the water circulation path;
inlet tubing coupled to the inlet port, the cool water supply device configured to pump water out of the vessel through the inlet tubing as the sole source of water to the cool water supply device;
outlet tubing coupled to the outlet port, the cool water supply device configured to pump water into the vessel through the outlet tubing;
a flow restrictor secured to an outlet tubing to regulate the back pressure in order to ensure proper pressure is maintained; and
a controller located within the cool water supply device in communication with the closed water circulation path and the refrigeration cycle, the controller including memory, which is accessible to a processor, the memory includes processor-executable instructions that, when executed cause the processor to execute instructions for measuring temperature via the thermostat, selectively activating the water pump, and selectively activating the refrigeration cycle to achieve a change in temperature of the water flowing through the closed water circulation path based on matching the desired temperature with the rate of flow and refrigeration cooling coefficient.

* * * * *